(12) United States Patent
Henry

(10) Patent No.: US 7,323,099 B2
(45) Date of Patent: Jan. 29, 2008

(54) TWO STAGE FLUID CATALYTIC CRACKING PROCESS FOR SELECTIVELY PRODUCING $C_2$ TO $C_4$ OLEFINS

(75) Inventor: Brian Erik Henry, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 299 days.

(21) Appl. No.: 10/993,036

(22) Filed: Nov. 19, 2004

(65) Prior Publication Data

US 2006/0108260 A1 May 25, 2006

(51) Int. Cl.
*C10G 51/02* (2006.01)
*C07C 4/06* (2006.01)

(52) U.S. Cl. ............... 208/67; 208/72; 208/74; 208/77; 208/158; 585/324; 585/648; 585/653

(58) Field of Classification Search ......... 208/67, 208/72, 74, 77, 152; 585/324, 648, 653
See application file for complete search history.

(56) References Cited

U.S. PATENT DOCUMENTS 4,871,446 A * 10/1989 Herbst et al. ............... 208/152
6,106,697 A * 8/2000 Swan et al. .................. 208/77

* cited by examiner

*Primary Examiner*—Glenn Caldarola
*Assistant Examiner*—Prem C. Singh

(57) ABSTRACT

A process for selectively producing $C_2$ to $C_4$ olefins from feedstock such as a gas oil or resid. The feedstock is reacted in a first stage comprising a fluid catalytic cracking unit wherein it is converted in the presence of a mixture of conventional large pore zeolitic catalyst and a medium pore zeolitic catalyst to reaction products, including a naphtha boiling range stream. The naphtha boiling range stream is introduced into a second stage where it is contacted with a catalyst containing from about 10 to about 50 wt. % of a crystalline zeolite having an average pore diameter less than about 0.7 nanometers at reaction conditions which include temperatures ranging from about 500 to about 650° C. and a hydrocarbon partial pressure from about 10 to about 40 psia (about 70 to about 280 kPa).

10 Claims, No Drawings

TWO STAGE FLUID CATALYTIC CRACKING PROCESS FOR SELECTIVELY PRODUCING $C_2$ TO $C_4$ OLEFINS

FIELD OF THE INVENTION

The present invention relates to a two-stage fluid catalytic cracking (FCC) process for selectively producing $C_2$ to $C_4$ olefins from a gas oil or resid.

BACKGROUND OF THE INVENTION

The need for low-emissions fuels has created an increased demand for light olefins used in alkylation, oligomerization, MTBE, and ETBE synthesis processes. In addition, a low cost supply of light olefins, particularly propylene, continues to be in demand to serve as feedstock for polyolefin production, particularly polypropylene production.

Fixed bed processes for light paraffin dehydrogenation have recently attracted renewed interest for increasing olefin production. However, these types of processes typically require relatively large capital investments and high operating costs. It is therefore advantageous to increase olefin yield using processes that require relatively small capital investment. It would be particularly advantageous to increase light olefin yield in catalytic cracking processes.

While conventional fluid catalytic cracking processes are suitable for producing conventional transportation fuels, these fuels are generally unable to meet the more demanding requirements of low emissions fuels and chemical feedstock production. To augment the volume of low emission fuels, it is desirable to increase the amounts of light olefins, such as propylene, iso- and normal butylenes, and isoamylene. The propylene, isobutylene, and isoamylene can be reacted with methanol to form methyl-propyl-ethers, methyl tertiary butyl ether (MTBE), and tertiary amyl methyl ether (TAME). In addition to enhancing the volume and octane number of gasoline, these components also reduce emissions. It is particularly desirable to increase the yield of ethylene and propylene, which are valuable chemical raw materials. Conventional fluid catalytic cracking does not produce large enough quantities of these light olefins, particularly ethylene. Consequently, there exists a need in the art for methods of producing larger quantities of ethylene and propylene for chemicals raw materials, as well as other light olefins for low-emissions transportation fuels, such as gasoline and distillates.

A problem inherent in producing olefin products using FCC units is that the process depends upon a specific catalyst balance to maximize production. In addition, even if a specific catalyst balance can be maintained to maximize overall olefin production, olefin selectivity is generally low due to undesirable side reactions, such as cracking, isomerization, aromatization, and hydrogen transfer reactions. Therefore, it is desirable to maximize olefin production in a process that allows a high degree of control over the selectivity of C2, C3, and C4 olefins.

SUMMARY OF THE INVENTION

A conventional FCC feed, preferably a gas oil or resid feed, is reacted in a first stage comprising a fluid catalytic cracking unit wherein it is converted in the presence of a mixture of a conventional large pore zeolitic catalyst and a medium pore zeolitic catalyst to reaction products, including a naphtha boiling range stream and a light vapor stream containing relatively high levels of propylene. The propylene is separated and collected and the naphtha boiling range stream is introduced into a second stage comprising a fluid catalytic cracking process unit containing a reaction zone, a stripping zone, a catalyst regeneration zone, and a fractionation zone. The naphtha boiling range stream is contacted in the reaction zone of this second stage with a catalyst containing from about 10 to about 50 wt. % of a crystalline medium pore zeolite having an average pore diameter less than about 0.7 nanometers at reaction conditions that include temperatures ranging from about 500 to about 650° C. and a hydrocarbon partial pressure from about 10 to about 40 psia (about 70 to about 280 kPa). Vapor products are collected overhead and the catalyst particles are passed through the stripping zone on the way to the catalyst regeneration zone. Volatiles are stripped from the medium pore zeolite catalyst with steam in the stripping zone and the stripped catalyst particles are sent to the catalyst regeneration zone where coke is burned from the catalyst, which is then recycled to the reaction zone.

One embodiment of the present invention comprises a process for producing polypropylene from olefins produced in a two stage process for selectively producing C2 to C4 olefins from a heavy hydrocarbon feed, the process comprising the steps of: (a) contacting a heavy hydrocarbon feed with a mixture of large-pore zeolitic catalytic cracking catalyst having an average pore diameter greater than about 0.7 nm and a medium pore zeolitic catalytic cracking catalyst having an average pore diameter less than about 0.7 nm in a first reaction stage comprising a fluid catalytic cracking unit to convert the heavy hydrocarbon feed to lower boiling reaction products; (b) fractionating said lower boiling reaction products into at least a propylene-rich vapor stream and a naphtha boiling range stream, the naphtha boiling range stream comprising between about 10 and about 30 wt. % paraffins and between about 15 and about 70 wt. % olefins; (c) collecting the propylene-rich fraction; (d) contacting the naphtha boiling range stream with a second catalyst comprising between about 10 and about 50 wt. % of a crystalline zeolite having an average pore diameter less than about 0.7 nm in a second reaction stage comprising a process unit comprising a reaction zone, a stripping zone, a second catalyst regeneration zone, and a fractionation zone, wherein the naphtha boiling range fraction is contacted with the second catalyst in the reaction zone at reaction conditions that include temperatures ranging from about 500 to about 650° C. and a hydrocarbon partial pressure from about 10 to about 40 psia (about 70 to about 280 kPa) and a catalyst to second stage feed weight ratio of about 4 to about 10, thereby producing a product including a C3 product of which propylene comprises at least about 75 mol. % of the total C3 product; (e) passing the second catalyst particles through the stripping zone wherein volatiles are stripped therefrom; (f) passing the stripped second catalyst particles to the regeneration zone where coke is combusted therefrom; (g) recycling the resulting hot second catalyst particles to the second stage reaction zone; (h) separating the propylene; and optionally, (i) polymerizing at least a fraction of the propylene to form polypropylene.

In another embodiment of the present invention the C3 product of the second stage has at least a 80 mol. % propylene content.

In another embodiment of the present invention propylene from the first stage is also polymerized to form polypropylene.

In another embodiment of the present invention the medium pore diameter catalyst in the first stage, the second stage, or both, is a ZSM-5 type catalyst.

In another embodiment of the present invention the second stage feed contains about 10 to about 30 wt. % paraffins, and from about 20 to about 70 wt. % olefins.

In yet another embodiment of the present invention the second stage reaction zone is operated at a temperature from about 525 to about 600° C.

DETAILED DESCRIPTION OF THE INVENTION

Catalytic cracking is an established and widely used process in the petroleum refining industry for converting hydrocarbonaceous feeds, such as petroleum oils of relatively high boiling point, to more valuable lower boiling products, including gasoline and middle distillates such as kerosene, jet fuel, and heating oil. The pre-eminent catalytic cracking process now in use is the fluid catalytic cracking process (FCC) in which a pre-heated feed is brought into contact with a hot cracking catalyst in the form of a fine powder, typically having a particle size of about 10 to about 300 microns, usually about 60 to 70 microns, for the desired cracking reactions to take place. During the cracking, coke and hydrocarbon material are deposited on the catalyst particles, resulting in a loss of catalyst activity and selectivity. The coked catalyst particles, and associated hydrocarbon material, are subjected to a stripping process, usually with steam, to remove as much of the hydrocarbon material as technically and economically feasible. The stripped particles, containing non-strippable coke, are removed from the stripper and sent to a regenerator where the coked catalyst particles are regenerated by contact with air, or a mixture of air and oxygen, at an elevated temperature, resulting in the combustion of the coke. The combustion is a strongly exothermic reaction that removes the coke and heats the catalyst to the temperatures appropriate for the endothermic cracking reaction. The process is carried out in an integrated unit comprising a fluidized cracking reactor, a stripper, a regenerator, and appropriate ancillary equipment. The catalyst is continuously circulated from the reactor, or reaction zone, to the stripper and then to the regenerator and back to the reactor. The circulation rate is typically adjusted relative to the feed rate of the oil to maintain a heat balanced operation in which the heat produced in the regenerator is sufficient for maintaining the cracking reaction with the circulating regenerated catalyst being used as the heat transfer medium. Typical fluid catalytic cracking processes are described in the monograph Fluid Catalytic Cracking with Zeolite Catalysts, Venuto, P. B. and Habib, E. T., Marcel Dekker Inc. N.Y. 1979, which is incorporated herein by reference. As described in this monograph, catalysts that are conventionally used are based on zeolites, especially the large pore synthetic faujasites, zeolites X and Y.

Typical heavy hydrocarbonaceous feeds to a catalytic cracker can generally be characterized as being a relatively high boiling oil or residuum, either alone or mixed with other fractions, also usually of a relatively high boiling point. The most common heavy hydrocarbonaceous feeds are gas oils, that is, high boiling, non-residual oils, with an initial boiling point usually above about 230° C., more commonly above about 350° C., with end points of up to about 620° C. Typical gas oils include straight run (atmospheric) gas oil, vacuum gas oil, and coker gas oils.

The heavy hydrocarbonaceous feed to the first stage of the present invention is preferably a hydrocarbon fraction having an initial ASTM boiling point of about 600° F. (315° C.). These hydrocarbon fractions include gas oils (including vacuum gas oils), thermal oils, residual oils, cycle stocks, topped whole crudes, tar sand oils, shale oils, synthetic fuels, heavy hydrocarbon fractions derived from the destructive hydrogenation of coal, tar, pitches, asphalts, and hydrotreated feeds derived from any of the foregoing.

The feed is reacted (converted) in a first stage, preferably in a fluid catalytic cracking reactor vessel where it is contacted with at least one of each of a large pore and a medium pore catalytic cracking catalyst that is continuously recycled to form lower boiling reaction products.

The feed can be mixed with steam or an inert gas at such conditions that will form a highly atomized stream of a vaporous hydrocarbon-catalyst mixture that undergoes reaction in the riser. Preferably, the reacting mixture flows through a riser into the reactor vessel. The reaction zone vessel is preferably operated at a temperature of about 800 to about 1200° F. (about 425 to about 650° C.) and a pressure of about 0 to 100 psig (100 to 790 kPa).

The catalytic cracking reaction is preferably quenched by separating the catalyst from the resulting vapor. The separated vapor comprises the cracked hydrocarbon product, and the separated catalyst contains coke deposited on the catalyst during the catalytic cracking reaction.

The coke is removed from the catalyst in a regenerator vessel by combusting the coke from the catalyst. Preferably, the coke is combusted at a temperature of about 900 to 1400° F. (about 480 to about 760° C.) and a pressure of about 0 to 100 psig (100 to 790 kPa). After the combustion step, the regenerated catalyst is recycled to the riser for contact with the primary feed.

The large pore catalyst used in the first stage of this invention can be any catalyst that is typically used to catalytically "crack" hydrocarbon feeds. It is preferred that the catalytic cracking catalyst be comprised of a crystalline tetrahedral framework oxide component. This component catalyzes the breakdown of primary products from the catalytic cracking reaction into clean products such as naphtha for fuels and olefins for chemical feedstocks. Preferably, the crystalline tetrahedral framework oxide component is selected from the group consisting of zeolites, tectosilicates, tetrahedral aluminophophates (ALPOs), and tetrahedral silicoaluminophosphates (SAPOs). More preferably, the crystalline framework oxide component is a zeolite.

Large pore zeolites that can be used in the first stage of the present invention include both natural and synthetic zeolites with average pore diameters greater than about 0.7 nm. Non-limiting examples of such zeolites include gmelinite, chabazite, dachiardite, clinoptilolite, faujasite, heulandite, analcite, levynite, erionite, sodalite, cancrinite, nepheline, lazurite, scolecite, natrolite, offretite, mesolite, mordenite, brewsterite, and ferrierite. Included among the synthetic zeolites are zeolites X, Y, A, L, ZK-4, ZK-5, B, E, F, H, J, M, Q, T, W, Z, alpha, beta, omega, and USY zeolites. USY zeolites are preferred.

The medium pore catalysts that are used in the first stage can be the same as those used in the second stage herein. Those medium pore catalysts, which are preferably zeolites and have an average pore diameter less than about 0.7 run are described below with respect to the second stage. The amount of medium pore catalyst that can be used in the first stage hereof is an effective amount. That is at least that amount needed to enhance the production of propylene in the first stage, but not so much that would be undesirable with respect to the intended product slate as to yield and selectivity. Such an amount will typically be from about 0.1 to about 10 wt. %, preferably from about 0.5 to about 3 wt. %, of medium pore zeolite crystals, based on the total weight of catalyst inventory for this first stage.

In general, aluminosilicate zeolites are effectively used in this invention. However, the aluminum and the silicon component can be substituted by other framework components. For example, the aluminum portion can be replaced by boron, gallium, titanium, or trivalent metal compositions that are heavier than aluminum. Germanium can be used to replace the silicon portion.

The catalytic cracking catalysts used in the first stage of this invention can further comprise an active porous inorganic oxide catalyst framework component and an inert catalyst framework component. Preferably, each component of the catalyst is held together with an inorganic oxide matrix component.

The active porous inorganic oxide catalyst framework component catalyzes the formation of primary products by cracking hydrocarbon molecules that are too large to fit inside the tetrahedral framework oxide component. The active porous inorganic oxide catalyst framework component of this invention is preferably a porous inorganic oxide that cracks a relatively large amount of hydrocarbons into lower molecular weight hydrocarbons as compared to an acceptable thermal blank. A low surface area silica (e.g., quartz) is one type of acceptable thermal blank. The extent of cracking can be measured in any of various ASTM tests such as the MAT (microactivity test, ASTM # D3907-8). Compounds such as those disclosed in Greensfelder, B. S., et al., Industrial and Engineering Chemistry, pp. 2573-83, November 1949, are desirable. Alumina, silica-alumina and silica-alumina-zirconia compounds are preferred.

The inert catalyst framework component densifies, strengthens, and acts as a protective thermal sink. The inert catalyst framework component used in this invention preferably has a cracking activity that is not significantly greater than the acceptable thermal blank. Kaolin and other clays and a-alumina, titania, zirconia, quartz, and silica are examples of preferred inert components.

The inorganic oxide matrix component binds the catalyst components together so that the catalyst product is hard enough to survive interparticle and reactor wall collisions. The inorganic oxide matrix can be made from an inorganic oxide sol or gel that is dried to "bind" the catalyst components together. Preferably, the inorganic oxide matrix will be comprised of oxides of silicon and aluminum. It is also preferred that separate alumina phases be incorporated into the inorganic oxide matrix. Species of aluminum oxyhydroxides-γ-alumina, boehmite, diaspore, and transitional aluminas such as α-alumina, β-alumina, γ-alumina, γ-alumina, ϵ-alumina, κ-alumina, and ρ-alumina can be employed. Preferably, the alumina species is an aluminum trihydroxide such as gibbsite, bayerite, nordstrandite, or doyelite. The matrix material may also contain phosphorous or aluminum phosphate.

It was thought that medium pore zeolites should not be used in the first stage of a two stage FCC process designed for producing high propylene yields. This is because a medium pore zeolite in the second stage would be expected to produce a more valuable propylene product, such as chemical grade propylene, than the dilute propylene produced in the first FCC stage thereof, if such first stage contained a medium pore zeolite.

It has unexpectedly been found that the use of relatively high concentrations of medium pore zeolites in a first stage FCC unit only slightly decreases the amount of chemical grade propylene produced in the second stage unit, while significantly increasing the amount of dilute propylene produced in the FCC unit. Chemical grade propylene, as opposed to dilute propylene, means a stream containing at least about 92 wt. % propylene, typically between about 92 wt. % and, 95 wt. %. Dilute, or refinery grade, propylene streams typically contain only about 50 to about 70 wt. % propylene.

A naphtha boiling range fraction of the lower boiling reaction product stream from the fluid catalytic cracking unit is used as the feed to a second reaction stage to selectively produce C2 to C4 olefins. This feed to the second reaction stage is preferably one that is suitable for producing the relatively high C2, C3, and C4 olefin yields. Such streams are those boiling in the naphtha range and containing from about 5 wt. % to about 35 wt. %, preferably from about 10 wt. % to about 30 wt. %, and more preferably from about 10 to about 25 wt. % paraffins, and from about 15 wt. %, preferably from about 20 wt. % to about 70 wt. % olefins. The second reaction stage feed may also contain naphthenes and aromatics. Naphtha boiling range streams are typically those having a boiling range from about 65° F. to about 430° F. (about 18° C. to about 225° C.), preferably from about 65° F. to about 300° F. (about 18° C. to about 150° C.). Naphtha streams from other sources in the refinery can be blended with the aforementioned feed and fed to this second reaction stage.

The second reaction stage occurs in a process unit comprising a reaction zone, a stripping zone, a catalyst regeneration zone, and a fractionation zone. The second reaction stage feed is fed into the reaction zone where it contacts a source of hot, second reaction stage catalyst ("second stage catalyst"). The hot second stage catalyst vaporizes and cracks the second reaction stage feed at a temperature from about 500 to about 650° C., preferably from about 500 to about 600° C. The cracking reaction deposits carbonaceous hydrocarbons, or coke, on the second stage catalyst, thereby deactivating the second stage catalyst. The cracked products are separated from the coked second stage catalyst and sent to a fractionator. The coked second stage catalyst is passed through the stripping zone where volatiles are stripped from the second stage catalyst particles with a stripping agent, such as steam. The stripping can be performed under low severity conditions to retain a greater fraction of adsorbed hydrocarbons for heat balance. The stripped second stage catalyst is then passed to the regeneration zone where it is regenerated by burning coke in the presence of an oxygen containing gas, preferably air. Decoking restores catalyst activity and simultaneously heats the catalyst to between about 650 and about 750° C. The hot second stage catalyst is then recycled to the reaction zone to react with fresh second reaction stage feed. Flue gas formed by burning coke in the regenerator may be treated for removal of particulates and for conversion of carbon monoxide. The cracked products from the reaction zone are sent to a fractionation zone where various products are recovered, particularly C2, C3, and C4 fractions.

While attempts have been made to increase light olefins yields in the FCC process unit itself, the practice of the present invention uses, as the second stage, its own distinct process unit, as previously described, which can receive naphtha from a suitable source in the refinery, preferably the FCC process unit. The second stage reaction zone is operated at process conditions that will maximize C2 to C4 olefin, particularly propylene, selectivity with relatively high conversion of C5+ olefins. Catalysts suitable for use in the second stage of the present invention are those which comprise a crystalline zeolite having an average pore diameter less than about 0.7 nanometers (nm), said crystalline zeolite comprising from about 10 wt. % to about 50 wt. % of the total fluidized catalyst composition. It is preferred that the crystalline zeolite be selected from the family of medium-pore-size (<0.7 nm) crystalline aluminosilicates, otherwise referred to as zeolites. Of particular interest are the medium-pore zeolites with a silica to alumina molar ratio of less than about 75:1, preferably less than about 50:1, and more preferably less than about 40:1, although some embodiments may incorporate silica to alumina ratios greater than 40:1. The pore diameter (also sometimes referred to as effective pore diameter) can be measured using standard adsorption techniques and hydrocarbonaceous compounds of known minimum kinetic diameters. See Breck, Zeolite Molecular Sieves, 1974 and Anderson et al., J. Catalysis 58, 114 (1979), both of which are incorporated herein by reference.

Medium-pore-size zeolites that can be used in the practice of the present invention are described in "Atlas of Zeolite Structure Types", eds. W. H. Meier and D. H. Olson, Butterworth-Heineman, Third Edition, 1992, which is hereby incorporated by reference. The medium-pore-size zeolites generally have a pore size from about 0.5 nm to about 0.7 nm and include for example, MFI, MFS, MEL, MTW, EUO, MTT, HEU, FER, and TON structure type zeolites (IUPAC Commission of Zeolite Nomenclature). Non-limiting examples of such medium-pore-size zeolites, include ZSM-5, ZSM-12, ZSM-22, ZSM-23, ZSM-34, ZSM-35, ZSM-38, ZSM-48, ZSM-50, silicalite, and silicalite 2. The most preferred is ZSM-5, which is described in U.S. Pat. Nos. 3,702,886 and 3,770,614. ZSM-11 is described in U.S. Pat. No. 3,709,979; ZSM-12 in U.S. Pat. No. 3,832,449; ZSM-21 and ZSM-38 in U.S. Pat. No. 3,948,758; ZSM-23 in U.S. Pat. No. 4,076,842; and ZSM-35 in U.S. Pat. No. 4,016,245. All of the above patents are incorporated herein by reference. Other suitable medium-pore-size materials include the silicoaluminophosphates (SAPO), such as SAPO-4 and SAPO-11 which is described in U.S. Pat. No. 4,440,871; chromosilicates; gallium silicates; iron silicates; aluminum phosphates (ALPO), such as ALPO-11 described in U.S. Pat. No. 4,310,440; titanium aluminosilicates (TASO), such as TASO-45 described in EP-A No. 229,295; boron silicates, described in U.S. Pat. No. 4,254,297; titanium aluminophosphates (TAPO), such as TAPO-11 described in U.S. Pat. No. 4,500,651; and iron aluminosilicates.

The medium-pore-size zeolites can include "crystalline admixtures" which are thought to be the result of faults occurring within the crystal or crystalline area during the synthesis of the zeolites. Examples of crystalline admixtures of ZSM-5 and ZSM-11 are disclosed in U.S. Pat. No. 4,229,424 which is incorporated herein by reference. The crystalline admixtures are themselves medium-pore-size zeolites and are not to be confused with physical admixtures of zeolites in which distinct crystals or crystallites of different zeolites are physically present in the same catalyst composite or hydrothermal reaction mixtures.

The second stage catalysts are held together with an inorganic oxide matrix component. The inorganic oxide matrix component binds the catalyst components together so that the catalyst product is hard enough to survive interparticle and reactor wall collisions. The inorganic oxide matrix can be made from an inorganic oxide sol or gel which is dried to "bind" the catalyst components together. Preferably, the inorganic oxide matrix is not catalytically active and is comprised of oxides of silicon and aluminum. Preferably, separate alumina phases are incorporated into the inorganic oxide matrix. Species of aluminum oxyhydroxides-γ-alumina, boehmite, diaspore, and transitional aluminas such as α-alumina, β-alumina, γ-alumina, δ-alumina, ε-alumina, κ-alumina, and ρ-alumina can be employed. Preferably, the alumina species is an aluminum trihydroxide such as gibbsite, bayerite, nordstrandite, or doyelite.

Preferred second stage process conditions include temperatures from about 500 to about 650° C., preferably from about 525 to about 600° C.; hydrocarbon partial pressures from about 10 to about 40 psia (about 70 to about 280 kPa), preferably from about 20 to about 35 psia (about 140 to about 245 kPa); and a second stage catalyst to naphtha (wt/wt) ratio from about 3 to about 12, preferably from about 4 to about 10, where the second stage catalyst weight is total weight of the second stage catalyst composite. Steam may be concurrently introduced with the naphtha stream into the reaction zone and may comprise up to about 50 wt. % of the second stage feed. Preferably, the second stage feed residence time in the reaction zone be less than about 10 seconds, for example from about 1 to about 10 seconds. The above conditions will be such that at least about 60 wt. % of the C5+ olefins in the naphtha stream are converted to C4-products and less than about 25 wt. %, preferably less than about 20 wt. %, of the paraffins are converted to C4-products, and that propylene comprises at least about 80 mol. %, preferably at least about 85 mol. %, more preferably at least about 90 mol. %, and most preferably greater than about 95 mol. %, of the total C3 reaction products with the weight ratio of propylene to total C2-products greater than about 2, preferably greater than about 2.5, and more preferably greater than about 3.5.

Preferably, ethylene comprises at least about 75 mol. %, preferably at least about 80 mol. %, and more preferably at least about 90 mol. %, of the C2 products, with the weight ratio of propylene:ethylene being greater than about 3, preferably greater than about 3.5, and more preferably greater than about 4.0. The "full range" C5+ naphtha product will be enhanced in both motor and research octanes relative to the naphtha feed. It is within the scope of this invention to pre-coke the second stage catalysts before introducing second stage feed to further improve the selectivity to propylene. It is also within the scope of this invention to feed an effective amount of single ring aromatics to the reaction zone of said second stage to improve the selectivity to propylene versus ethylene. The aromatics may be from an external source such as a reforming process unit or they may consist of heavy naphtha recycle product from the instant process.

The first stage and second stage regenerator flue gases are combined in one embodiment of this invention, and the light ends or product recovery section may also be shared with suitable hardware modifications. High selectivity to the desired light olefins products in the second stage lowers the investment required to revamp existing light ends facilities for additional light olefins recovery. The composition of the catalyst of the first stage is typically selected to maximize hydrogen transfer. In this manner, the second stage feed may be optimized for maximum C2, C3, and C4 olefins yields with relatively high selectivity using the preferred second stage catalyst and operating conditions. Total high value light olefin products from the combined two stages include those generated with relatively low yield in the first stage plus those produced with relatively high yield in the second stage.

The following examples are presented for illustrative purposes only and are not to be taken as limiting the present invention in any way.

EXAMPLES 1-13

The following examples illustrate the impact of process operating conditions on propylene purity with samples of cat naphtha cracked over ZCAT-40 (a catalyst that contains ZSM-5) which had been steamed at 1500° F. (about 815° C.) for 16 hours to simulate commercial equilibrium. Comparison of Examples 1 and 2 show that increasing catalyst to oil wt./wt. ratio improves propylene yield, but sacrifices propylene purity. Comparison of Examples 3 and 4 and 5 and 6 shows reducing oil partial pressure greatly improves propylene purity without compromising propylene yield. Comparison of Examples 7 and 8 and 9 and 10 shows increasing temperature improves both propylene yield and purity. Comparison of Examples 11 and 12 shows decreasing catalyst residence time improves propylene yield and purity. Example 13 shows an example where both high propylene yield and purity are obtained at a reactor temperature and catalyst to oil ratio that can be achieved using a conventional FCC reactor/regenerator design for the second stage.

Examples 14-17

The cracking of olefins and paraffins contained in naphtha streams (e.g. FCC naphtha, coker naphtha) over small- or medium-pore zeolites such as ZSM-5 can produce significant amounts of ethylene and propylene. The selectivity to ethylene or propylene and selectivity to propylene over propane vary as a function of catalyst and process operating conditions. It has been found that propylene yield can be increased by co-feeding steam along with naphtha to the reactor. The catalyst may be ZSM-5 or other small or medium-pore zeolites. Table 2 below illustrates the increase in propylene yield when 5 wt. % steam is co-fed with an FCC naphtha containing 38.8 wt. % olefins. Although propylene yield is increased, the propylene purity is diminished. Thus, other operating conditions may need to be adjusted to maintain the targeted propylene selectivity.

TABLE 1

| Example | Feed Olefins, wt % | Temp. °C. | Cat/Oil, wt./wt. | Oil, psia | Oil Res. Time, sec | Cat Res. Time, sec | Wt. % $C_3^=$ |
|---|---|---|---|---|---|---|---|
| 1 | 38.6 | 566 | 4.2 | 36 | 0.5 | 4.3 | 11.4 |
| 2 | 38.6 | 569 | 8.4 | 32 | 0.6 | 4.7 | 12.8 |
| 3 | 22.2 | 510 | 8.8 | 18 | 1.2 | 8.6 | 8.2 |
| 4 | 22.2 | 511 | 9.3 | 38 | 1.2 | 5.6 | 6.3 |
| 5 | 38.6 | 632 | 16.6 | 20 | 1.7 | 9.8 | 16.7 |
| 6 | 38.6 | 630 | 16.6 | 13 | 1.3 | 7.5 | 16.8 |
| 7 | 22.2 | 571 | 5.3 | 27 | 0.4 | 0.3 | 6.0 |
| 8 | 22.2 | 586 | 5.1 | 27 | 0.3 | 0.3 | 7.3 |
| 9 | 22.2 | 511 | 9.3 | 38 | 1.2 | 5.6 | 6.3 |
| 10 | 22.2 | 607 | 9.2 | 37 | 1.2 | 6.0 | 10.4 |
| 11 | 22.2 | 576 | 18.0 | 32 | 1.0 | 9.0 | 9.6 |
| 12 | 22.2 | 574 | 18.3 | 32 | 1.0 | 2.4 | 10.1 |
| 13 | 38.6 | 606 | 8.5 | 22 | 1.0 | 7.4 | 15.0 |

| Example | Wt. % Propane | Propylene Purity, % | Wt. % $C_2^=$ | Wt. % $C_2^-$ | Ratio of $C_3^=$ to $C_2^=$ | Ratio of $C_3^=$ to $C_2^-$ | Wt. % $C_3^=$ |
|---|---|---|---|---|---|---|---|
| 1 | 0.5 | 95.8% | 2.35 | 2.73 | 4.9 | 4.2 | 11.4 |
| 2 | 0.8 | 94.1% | 3.02 | 3.58 | 4.2 | 3.6 | 12.8 |
| 3 | 1.1 | 88.2% | 2.32 | 2.53 | 3.5 | 3.2 | 8.2 |
| 4 | 1.9 | 76.8% | 2.16 | 2.46 | 2.9 | 2.6 | 6.3 |
| 5 | 1.0 | 94.4% | 6.97 | 9.95 | 2.4 | 1.7 | 16.7 |
| 6 | 0.6 | 96.6% | 6.21 | 8.71 | 2.7 | 1.9 | 16.8 |
| 7 | 0.2 | 96.8% | 1.03 | 1.64 | 5.8 | 3.7 | 6.0 |
| 8 | 0.2 | 97.3% | 1.48 | 2.02 | 4.9 | 3.6 | 7.3 |
| 9 | 1.9 | 76.8% | 2.16 | 2.46 | 2.9 | 2.6 | 6.3 |
| 10 | 2.2 | 82.5% | 5.21 | 6.74 | 2.0 | 1.5 | 10.4 |
| 11 | 4.0 | 70.6% | 4.99 | 6.67 | 1.9 | 1.4 | 9.6 |
| 12 | 1.9 | 84.2% | 4.43 | 6.27 | 2.3 | 1.6 | 10.1 |
| 13 | 0.7 | 95.5% | 4.45 | 5.76 | 3.3 | 2.6 | 15.0 |

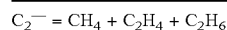
$C_2^- = CH_4 + C_2H_4 + C_2H_6$

Examples 1, 2, 7, and 8 show that $C_3^=:C_2^=$ greater than 4 and $C_3^=:C_2^-$ greater than 3.5 can be achieved by selection of suitable reactor conditions.

TABLE 2

| Example | Steam Co-feed | Temp. C. | Cat/Oil | Oil psia | Oil Res. Time, sec | Cat Res. Time, sec | Wt % Propylene | Wt % Propane | Propylene Purity, % |
|---|---|---|---|---|---|---|---|---|---|
| 14 | No | 630 | 8.7 | 18 | 0.8 | 8.0 | 11.7 | 0.3 | 97.5% |
| 15 | Yes | 631 | 8.8 | 22 | 1.2 | 6.0 | 13.9 | 0.6 | 95.9% |
| 16 | No | 631 | 8.7 | 18 | 0.8 | 7.8 | 13.6 | 0.4 | 97.1% |
| 17 | Yes | 632 | 8.4 | 22 | 1.1 | 6.1 | 14.6 | 0.8 | 94.8% |

Light olefins resulting from the preferred process may be used as feeds for processes such as oligimerization, polymerization, co-polymerization, ter-polymerization, and related processes (hereinafter "polymerization") to form macromolecules. Such light olefins may be polymerized both alone and in combination with other species, in accordance with polymerization methods known in the art. In some cases it may be desirable to separate, concentrate, purify, upgrade, or otherwise process the light olefins prior to polymerization. Propylene and ethylene are preferred polymerization feeds. Polypropylene and polyethylene are preferred polymerization products made therefrom.

Example 18

The following paper example presents predicted yields for a 100,000 B/d first stage FCC unit with an adjoining second stage unit operated under conditions to maximize propylene.

TABLE 3

| Catalyst in 1st Stage FCC | No ZSM-5 | 7 wt. % ZSM-5 additive |
|---|---|---|
| Wt % $C_3^=$ from 1$^{st}$ Stage | 4.00 | 6.33 |
| Wt % $C_5$-$C_7$ from 1$^{st}$ Stage (feed for 2$^{nd}$ stage) | 26.9 | 25.4 |
| Wt. % Olefins in 1$^{st}$ Stage $C_5$-$C_7$ | 46.2 | 45.9 |
| 2$^{nd}$ Stage $C_3^=$ yield as a Wt % of 2$^{nd}$ Stage Feed | 15.65 | 15.58 |
| 2$^{nd}$ Stage $C_3^=$ yield as a Wt % of 1$^{st}$ Stage Feed | 4.21 | 3.96 |
| Dilute Grade $C_3^=$ from 1$^{st}$ Stage, kilotons/year | 213 | 336 |
| Chem Grade $C_3^=$ from 2$^{nd}$ Stage, kilotons/year | 224 | 210 |
| Sum of 1$^{st}$ and 2$^{nd}$ Stage $C_3^=$, kilotons/year | 437 | 546 |

Thus, the addition of 7 wt. % of a ZSM-5 additive containing 25 wt. % ZSM-5 to the first stage FCC will result in a 58 wt. % increase in the amount of dilute propylene produced with only a 6 wt. % decrease in the amount of chemical grade second stage propylene. The overall amount of propylene produced will increase by 25%. This example was calculated based on the ZSM-5 catalyst which is commercially available and marketed by Grace Davison under the tradename "OlefinsMax."

What is claimed is:

1. A two stage process for selectively producing $C_2$ to $C_4$ olefins from a heavy hydrocarbonaceous feed, the process comprising the steps of:
   a) contacting a heavy hydrocarbonaceous feed with a mixture of a large-pore zeolitic catalytic cracking catalyst having an average pore diameter greater than about 0.7 nm and a medium-pore zeolitic catalytic cracking catalyst having an average pore diameter less than about 0.7 nm in a first reaction stage comprising a fluid catalytic cracking unit to convert said heavy hydrocarbonaceous feed to lower boiling reaction products;
   b) fractionating said lower boiling reaction products into at least a propylene-rich vapor stream and a naphtha boiling range fraction, the naphtha boiling range fraction comprising between about 10 and about 30 wt. % paraffins and between about 15 and about 70 wt. % olefins;
   c) collecting said propylene-rich vapor stream;
   d) contacting said naphtha boiling range fraction with a second catalyst comprising between about 10 and about 50 wt. % of a crystalline zeolite having an average pore diameter less than about 0.7 nm in a second reaction stage comprising a process unit comprising a reaction zone, a stripping zone, a second catalyst regeneration zone, and a fractionation zone, wherein the naphtha boiling range fraction is contacted with the second catalyst in the reaction zone at reaction conditions which include temperatures ranging from about 500 to about 650° C. and a hydrocarbon partial pressure from about 10 to about 40 psia (about 70 to about 280 kPa) and a catalyst to second stage feed weight ratio of about 4 to about 10, and wherein propylene comprises at least about 75 mol. % of the total $C_3$ product;
   e) collecting the $C_3$ product overhead;
   f) passing the second catalyst particles through the stripping zone wherein volatiles are stripped therefrom with steam;
   g) passing the stripped second catalyst particles to the regeneration zone where coke is combusted from the second catalyst resulting in hot catalyst particles;
   h) recycling the hot second catalyst particles to the second stage reaction zone; and
   i) separating the propylene from the $C_3$ product.

2. The process of claim 1 wherein the medium-pore zeolites used in the first stage, the second stage, or both, are selected from the group consisting of ZSM-5 and ZSM-11.

3. The process of claim 2 wherein the reaction temperature of the second stage is from about 500 to about 600° C.

4. The process of claim 3 wherein at least about 60 wt. % of the $C_5$+olefins in the naphtha boiling range feed are convened to $C_4$-products and less than about 25 wt. % of the paraffins are convened to $C_4$-products.

5. The process of claim 4 wherein the weight ratio of propylene to total $C_2$-products is greater than about 3.5.

6. The process of claim 1 wherein the large pore zeolitic catalytic cracking catalyst of the first stage is selected from the group consisting of gmelinite, chabazite, dachiardite, clinoptilolite, faujasite, heulandite, analcite, levynite, erionite, sodalite, cancrinite, nepheline, lazurite, scolecite, natrolite, offretite, mesolite, mordenite, brewsterite, ferrierite and the synthetic zeolites X, Y, A, L, ZK-4, ZK-5, H, B, E, F, H, J, M, Q, T, W, Z, alpha, beta, omega, and USY.

7. The process of claim 6 wherein the large pore zeolitic catalytic cracking catalyst is a USY zeolite.

8. The process according to claim 1 wherein propylene comprises at least about 80 mol. % of the total second stage $C_3$ products.

9. The process according to claim 8 wherein propylene comprises at least about 90 mol. % of the total second stage $C_3$ products.

10. The process of claim 1 wherein the propylene of the first stage, the second stage, or both is polymerized to polypropylene.

* * * * *